(12) United States Patent
Kleinekofort (10) Patent No.: US 6,221,040 B1
(45) Date of Patent: Apr. 24, 2001

(54) METHOD OF MONITORING A VASCULAR ACCESS AND AN APPARATUS FOR EXTRACORPOREAL TREATMENT OF BLOOD WITH A DEVICE FOR MONITORING THE VASCULAR ACCESS

(75) Inventor: Wolfgang Kleinekofort, Kelkheim (DE)

(73) Assignee: Fresenius Medical Care Deutschland, Hamburg (DE)

( * ) Notice: Subject to any disclaimer, the term of this patent is extended or adjusted under 35 U.S.C. 154(b) by 0 days.

(21) Appl. No.: 09/420,624

(22) Filed: Oct. 20, 1999

(30) Foreign Application Priority Data

Oct. 20, 1998 (DE) .............................................. 198 48 235

(51) Int. Cl.$^7$ .................................................. A61M 31/00
(52) U.S. Cl. .............................................. 604/65; 604/4.01
(58) Field of Search ................................. 604/65, 66, 67, 604/4.01, 5.01, 6.01, 500; 494/18, 21, 35, 45, 43, 41

(56) References Cited

U.S. PATENT DOCUMENTS

| | | | |
|---|---|---|---|
| 5,720,716 | * | 2/1998 | Blakeslee et al. .................. 604/4.01 |
| 5,738,644 | * | 4/1998 | Holmes et al. ..................... 604/4.01 |
| 5,910,252 | * | 6/1999 | Truitt et al. ............................ 604/65 |

FOREIGN PATENT DOCUMENTS

| | | |
|---|---|---|
| 40 24 434 | 2/1992 | (DE) . |
| 197 34 002 | 9/1998 | (DE) . |
| 0 611 228 | 8/1994 | (EP) . |
| WO 97/10013 | 3/1997 | (WO) . |

* cited by examiner

Primary Examiner—John D. Yasko
(74) Attorney, Agent, or Firm—Kenyon & Kenyon (57) ABSTRACT

A method and device for monitoring a vascular access during a dialysis treatment in which the pressures in both the arterial and venous branches of the extracorporeal blood system are monitored by pressure sensors. Characteristic values for the condition of the vascular access are calculated in a computer unit from the pressures in the arterial and venous branches of the extracorporeal system, and these values are analyzed in an analyzer unit to detect a defective vascular access.

14 Claims, 6 Drawing Sheets

| Cause | $P_{art.}$ | $P_{ven.}$ | $P_s$ |
|---|---|---|---|
| 1. Drop in patient's blood pressure | ↓ | ↓ | ↓ |
| 2. Increase in patient's blood pressure | ↑ | ↑ | ↑ |
| 3. Increase in viscosity of the blood | ↓ | ↑ | ↓ |
| 4. Decline in viscosity of the blood | ↑ | ↓ | ↑ |
| 5. Increase in $Q_B$ | ↓ | ↑ | ↓ |
| 6. Reduction in $Q_B$ | ↑ | ↓ | ↑ |
| 7. Change in position of the patient upward | ↑ | ↑ | ↑ |
| 8. Change in position of the patient downward | ↓ | ↓ | ↓ |
| 9. Blood leak in the arterial tubing system | ↑ | → | ↑ |
| 10. Blood leak in the venous tubing system | → | ↓ | ↓ |
| 11. Arterial cannula slips out | ↑ | → | ↑ |
| 12. Venous cannula slips out | ↓ | ↓ | ↓ |

Influences contributing to the change in pressures in the extracorporeal system

↑ : increase

↓ : decrease

→ : no change

Fig. 1

| ΔP | $\sum_N d(P_s)$ | $\sum_N d(\Delta P)$ | Comments |
|---|---|---|---|
| → | − | 0 | |
| → | + | 0 | |
| ↑ | − | + | |
| ↓ | + | − | |
| ↑ | − | + | Figure 4 |
| ↓ | + | − | Figure 4 |
| → | + | 0 | |
| → | − | 0 | Figure 5 |
| ↑ | + | + | Protected by existing protective systems |
| ↓ | − | − | Figure 6; inadequately protected |
| ↑ | + | + | Protected by existing protective systems |
| ↓ | − | − | Figure 6; inadequately protected |

METHOD OF MONITORING A VASCULAR ACCESS AND AN APPARATUS FOR EXTRACORPOREAL TREATMENT OF BLOOD WITH A DEVICE FOR MONITORING THE VASCULAR ACCESS

FIELD OF THE INVENTION

The present invention relates to a method of monitoring a vascular access during an extracorporeal blood treatment, in particular a chronic blood purification therapy such as hemodialysis, hemofiltration and hemodiafiltration and an apparatus for extracorporeal blood treatment, in particular for hemodialysis, hemofiltration and hemodiafiltration with a device for monitoring the vascular access.

BACKGROUND OF THE INVENTION

With the known methods of chronic blood purification therapy such as hemodialysis, hemofiltration and hemodiafiltration, the patient's blood is passed through an extracorporeal system. Arteriovenous fistulas, vascular implants and/or various catheters are used as access to the patient's vascular system. Typical flow rates in a vascular access are in the range of 1100 mL/min. The patient is usually connected to the extracorporeal system by dialysis cannulas which are used to tap into the fistula or the vascular implant.

If the connection between the extracorporeal system and the vascular system becomes undone or a blood leak occurs in the extracorporeal system, the patient can be prevented from bleeding to death only if the extracorporeal blood flow is stopped within a few minutes. Therefore, extracorporeal blood systems are generally equipped with protective systems to constantly monitor the arterial and venous pressure ($P_{art}$ and $P_{ven}$) within the system as well as the admission of air into the extracorporeal system.

In the event of an alarm, the blood treatment is stopped, the venous clamp is closed and acoustic and optical warning signals are triggered. The protective system based on the pressure measurement responds when the arterial or venous pressure in the extracorporeal system changes by more than ±60 mm Hg. The alarm limits are selected so that a change in the position of the patient does not trigger an alarm.

If the connection between the patient and machine becomes undone at the arterial connection, i.e., at the cannula establishing the patient's blood flow to the extracorporeal system, the pressure-based protective system on the machine responds rapidly, as explained below. The dialysis cannula presents the greatest flow resistance in the extracorporeal system. When air is drawn through the cannula into the arterial vacuum system of the extracorporeal system, the flow resistance of the cannula drops by a factor of $10^3$ in proportion to the difference in density between the blood and air. Thus, the arterial vacuum in the extracorporeal system collapses suddenly.

However, the response of the pressure-based protective system is not always guaranteed in the case when the venous cannula has become detached from the vascular access. On the venous side, the purified blood is supplied to the patient at an excess pressure, with the venous excess pressure being proportional to the delivery rate of the blood pump. This prevents penetration of air through the cannula into the extracorporeal system, which would be the case on the arterial vacuum side. Therefore, the flow resistance of the venous cannula does not change, and the venous pressure on the machine end drops only by the amount of the pressure in the patient's vascular access. Thus, the change in venous pressure in the extracorporeal system is usually too low to trigger the pressure-based protective system to respond. The additional hydrostatic pressure difference between the venous pressure sensor and the cannula triggers a machine alarm only when the venous cannula is definitely below the fistula after slipping out of the vascular access.

In the case of a blood leak in the venous tubing system, it may also occur that the resulting venous pressure drop is not sufficient to guarantee that the existing pressure-based protective system will be triggered.

In addition to the above method, where the pressure in the arterial branch of the extracorporeal system is monitored to detect whether the arterial cannula has slipped out, and where the pressure in the venous branch of the extracorporeal system is monitored independently of the pressure monitoring in the arterial branch to detect whether the venous cannula has slipped out, there are known monitoring systems that monitor pressure pulses propagating in the extracorporeal system.

International Patent No. WO 97/10013 describes a dialysis machine having such a monitoring system which monitors the pressure pulses in the venous blood line produced by the blood pump in the arterial blood line.

SUMMARY OF THE INVENTION

An object of the present invention is to provide a method of monitoring a vascular access during an extracorporeal blood treatment that allows reliable detection of the venous cannula slipping out of the vascular access as well as reliable detection of a blood leak in the venous branch of the extracorporeal system while also requiring a minimum of equipment. This object is achieved by a method of calculating certain characteristic values from the pressure in a patient's extracorporeal blood path during treatment and comparing these characteristic values to predetermined ranges for these values. The method includes monitoring a vascular access during an extracorporeal blood treatment, wherein a patient's blood is provided from the vascular access to an extracorporeal blood path. The extracorporeal blood path includes an arterial line which is in fluid communication with an arterial access at one end and the inlet of a blood treatment device at the other end. The blood path also includes a venous line extending from and in fluid communication with an outlet in the blood treatment device and in fluid communication with a venous vascular access. According to the method, the fluid pressure within the arterial and venous lines is measured and from these measured values characteristic values for the integrity of the vascular access are calculated. The integrity of the vascular access is determined by comparing the characteristic values to ranges of predetermined values.

Another object of the present invention is to create an apparatus for extracorporeal blood treatment with a device for monitoring a vascular access that detects whether the venous cannula has slipped out of the vascular access as well as whether there is any blood leak in the venous branch of the extracorporeal system with a high reliability while requiring a minimum of additional equipment. This object is achieved by a system that will calculate certain characteristic values from the pressure in a patient's extracorporeal blood path during treatment and compare the calculated characteristic values to predetermined ranges for these values. The system according to the invention includes an extracorporeal blood path having an arterial line which is in fluid connection with an arterial vascular access and an inlet to a blood treatment device. The system further includes a venous line which is in fluid connection with an outlet of the blood treatment device and a venous vascular access. The system also includes an arterial fluid pressure sensor connected to the arterial line that is adapted for measuring pressure within the arterial line and a venous fluid pressure sensor connected to the venous line that is adapted for measuring pressure within the venous line. The system further includes a computer unit connected to the arterial and venous pressure sensors, which is adapted for generating characteristic values related to the integrity of the vascular access from measured arterial and venous pressures. Also provided in the system according to the invention is an analyzer unit that is adapted for comparing the calculated characteristic values to predetermined ranges values in order to assess the integrity of the vascular access.

The method according to the present invention can be designed as a protective system integrated into the machine, using sensors that are already present in the known blood treatment machines. Thus, the only required change in the machine to implement the protective system is modifying the machine control.

The method according to the present invention is based on the fact that both the pressure in the arterial branch and the pressure in the venous branch of the extracorporeal system are monitored to detect when the venous cannula slips out of the vascular access or when there is a blood leak in the venous branch of the extracorporeal system. Values characteristic of the condition of the vascular access are calculated from the pressure in the arterial and venous branches of the extracorporeal system and are then analyzed to detect a defective vascular access.

With the method according to the present invention, it is possible to reliably detect not only whether the venous cannula has slipped out or whether there is a blood leak in the venous branch of the extracorporeal system, but also whether the arterial cannula has slipped out and whether there is a blood leak in the arterial branch of the extracorporeal system.

The method according to the present invention can also be combined with other methods of detecting a defective vascular access. This further increases the reliability of the monitoring system.

For the case when the vascular access is defective, an acoustic and/or a visual alarm is preferably triggered. In addition, the blood flow in the extracorporeal system can be interrupted to prevent any blood loss. The blood flow can be interrupted using a suitable apparatus for extracorporeal blood treatment, such as by stopping the blood pump arranged in the extracorporeal system and/or closing a safety valve, such as a hose clamp arranged in the extracorporeal system.

Monitoring for a defective vascular access with the method according to the present invention is possible not only in an apparatus for hemodialysis, hemofiltration or hemodiafiltration, but also in cell separators in which a donor's blood is centrifuged in an extracorporeal system, thereby separating it into its components.

The method according to the present invention for monitoring a vascular access and an apparatus for extracorporeal blood treatment with a device for monitoring the vascular access are explained in greater detail below with respect to the drawings and on the basis of a preferred embodiment.

DESCRIPTION OF THE PREFERRED EMBODIMENT

During extracorporeal blood treatment, the arterial and venous pressures ($P_{art}$ and $P_{ven}$) in the extracorporeal system are measured with a frequency f, and the sum $P_S$ of the venous and arterial pressures is formed (equation 1).

$$P_S = P_{ven} + P_{art} \quad \text{(equation 1)}$$

$P_{art}$ = measured arterial pressure in the extracorporeal system $P_{ven}$ = measured venous pressure in the extracorporeal system In addition, the pressure difference ΔP between the venous and arterial pressures is also calculated:

$$\text{delta } P = P_{ven} - P_{art} \quad \text{(equation 2)}$$

The change in the sum of the arterial and venous pressures is given by:

$$d(P_S) = P_{SN} - P_{SN-1} \quad \text{(equation 3)}$$

$P_{SN}$ = instantaneous measured total pressure
$P_{SN-1}$ = previous measured total pressure The change in the pressure difference is given as follows:

$$d(\text{delta } P) = \text{delta } P_N - \text{delta } P_{N-1} \quad \text{(equation 4)}$$

delta $P_N$ = instantaneous measured pressure difference
delta $P_{N-1}$ = previous measured pressure difference A defective vascular access is deduced when the following conditions are met for N successive measurements:

a)

$$\Sigma N \, d(P_S) \text{ is negative and is less than a threshold value } M_1 \quad \text{(equation 5)}$$

b)

$$\Sigma N \, d(\Delta P) \text{ is negative and is less than a threshold value } M_2 \quad \text{(equation 6)}$$

In this case, either the venous cannula has slipped out of the vascular access, or there is a blood leak in the venous branch of the extracorporeal system.

Figure 1:
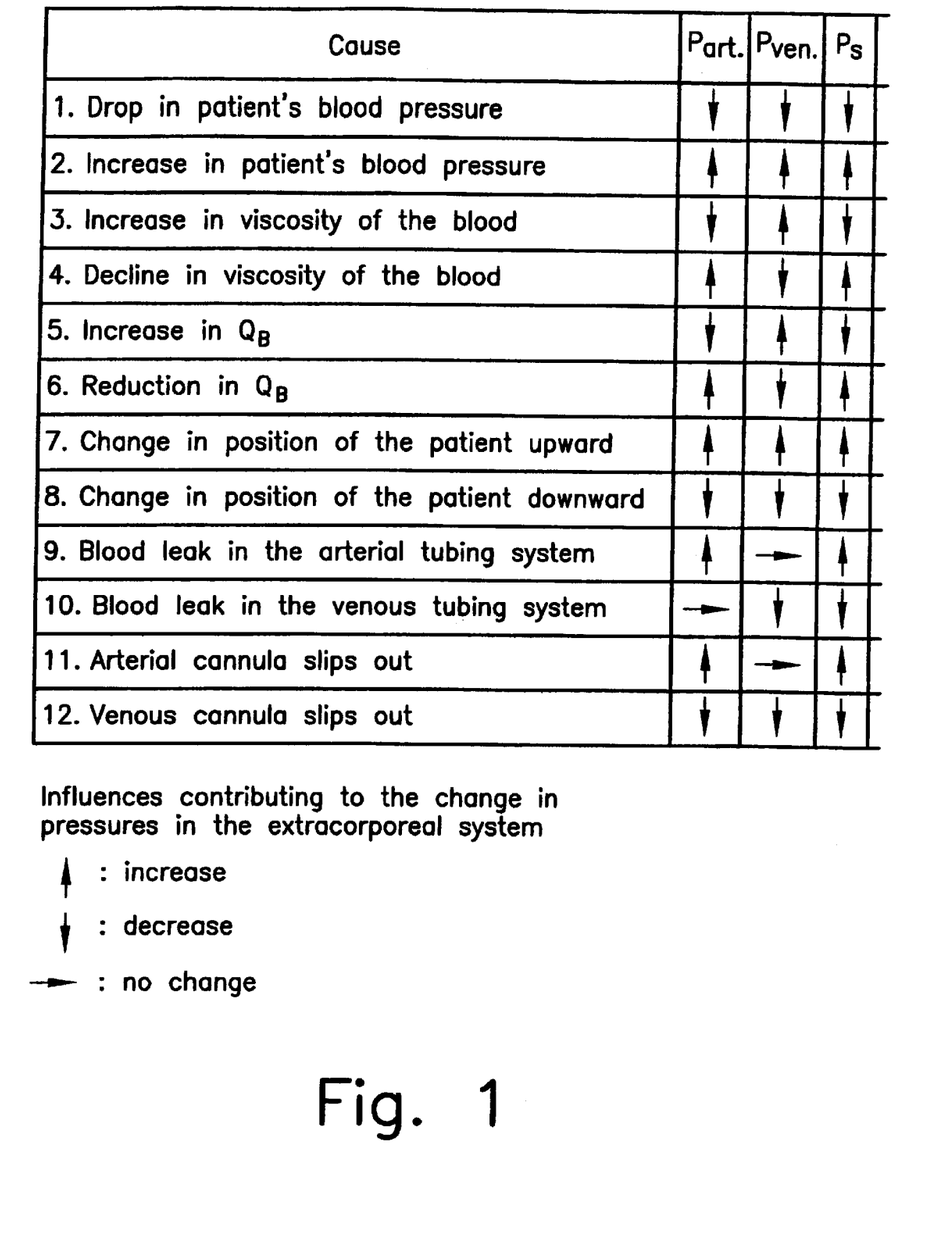
FIG. 1 is a table showing the influences that can contribute to a change in the pressure in the arterial and venous branches of the extracorporeal system.

The table (FIG. 1) shows influences that can contribute toward a change in the venous and arterial pressure in the extracorporeal system. This table shows that in addition to detecting when the venous cannula slips out, or whether there is a blood leak in the venous branch of the extracorporeal system, it is also possible to detect when the arterial cannula slips out or if there is a blood leak in the arterial branch of the extracorporeal system.

It can be deduced that the arterial cannula has slipped out or that there is a blood leak in the arterial branch of the extracorporeal system if the following conditions are met:

a)
$$\Sigma N\ d(P_S) \text{ is positive and is greater than a threshold value } M_3 \quad \text{(equation 7)}$$

b)
$$\Sigma N\ d(\Delta P) \text{ is positive and is greater than a threshold value } M_4 \quad \text{(equation 8)}$$

Figure 2:
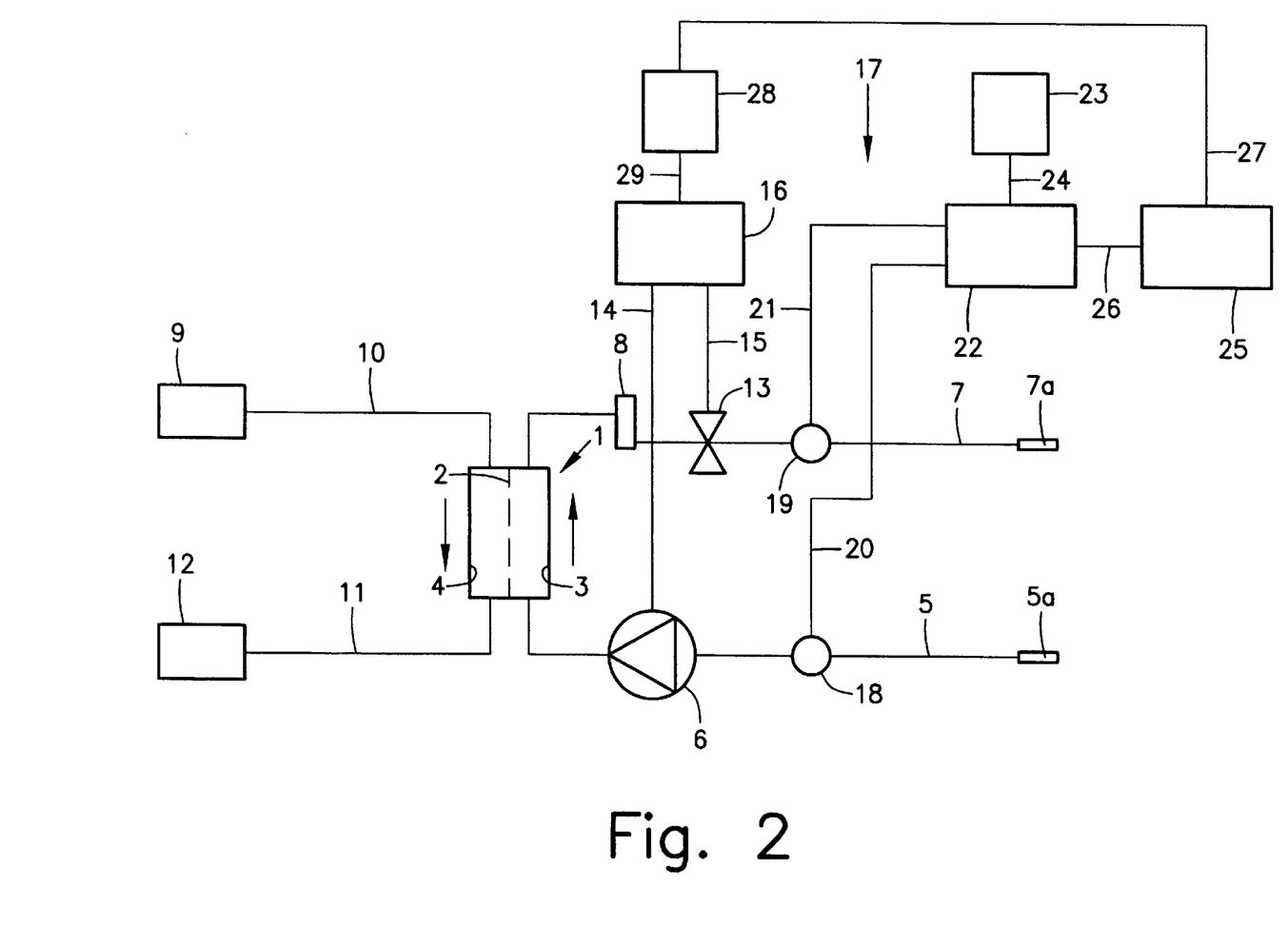
FIG. 2 depicts one embodiment of an apparatus for extracorporeal blood treatment with a device for monitoring the vascular access in a simplified schematic diagram.

FIG. 2 shows a simplified schematic diagram of a dialysis machine with a device for monitoring the vascular access.

The dialysis machine has a dialyzer 1 which is subdivided by a semipermeable membrane 2 into a blood chamber 3 and a dialysis fluid chamber 4. An arterial blood line 5 is connected to the inlet of the blood chamber and to a peristaltic blood pump 6. Downstream from blood chamber 3, a venous blood line 7 leads from the outlet of the blood chamber to the patient. A drip chamber 8 is connected to the venous blood line 7. Cannulas 5a, 7a are inserted into the patient and connected to the ends of the arterial and venous blood lines 5, 7. The arterial and venous blood lines preferably are part of a tubing system designed to be disposable.

Fresh dialysis fluid is prepared and located at a dialysis fluid source 9. A dialysis fluid inlet line 10 leads from dialysis fluid source 9 to the inlet of the dialysis fluid chamber 4 of dialyzer 1, while dialysis fluid outlet line 11 leads from the outlet of the dialysis fluid chamber to a drain 12.

The dialysis machine may also have other components, such as a balancing device and an ultrafiltration device, etc., which are not shown here for the sake of simplicity.

To interrupt the blood flow, a cutoff clamp 13 which is operated electromagnetically is provided on venous blood line 7 downstream from drip chamber 8. Arterial blood pump 6 and venous cutoff clamp 13 are controlled by a control unit 16 over control lines 14, 15.

Device 17 for monitoring the vascular access has an arterial pressure sensor 18 monitoring pressure in arterial blood line 5 and a venous pressure sensor 19 monitoring pressure in venous blood line 7. The measured values of pressure sensors 18, 19 are sent over data lines 20, 21 to a computer unit 22 which calculates characteristic values for the condition of the vascular access from the measured values. Interim results obtained in the calculation can be stored in a memory unit 23 connected by a data line 24 to computer unit 22. To analyze the characteristic values for the vascular access, the monitoring unit has an analyzer unit 25 which is connected to the computer unit by a data line 26. Analyzer unit 25 is connected by a control line 27 to an alarm unit 28, which is in turn connected by a control line 29 to control unit 16.

Figure 3:
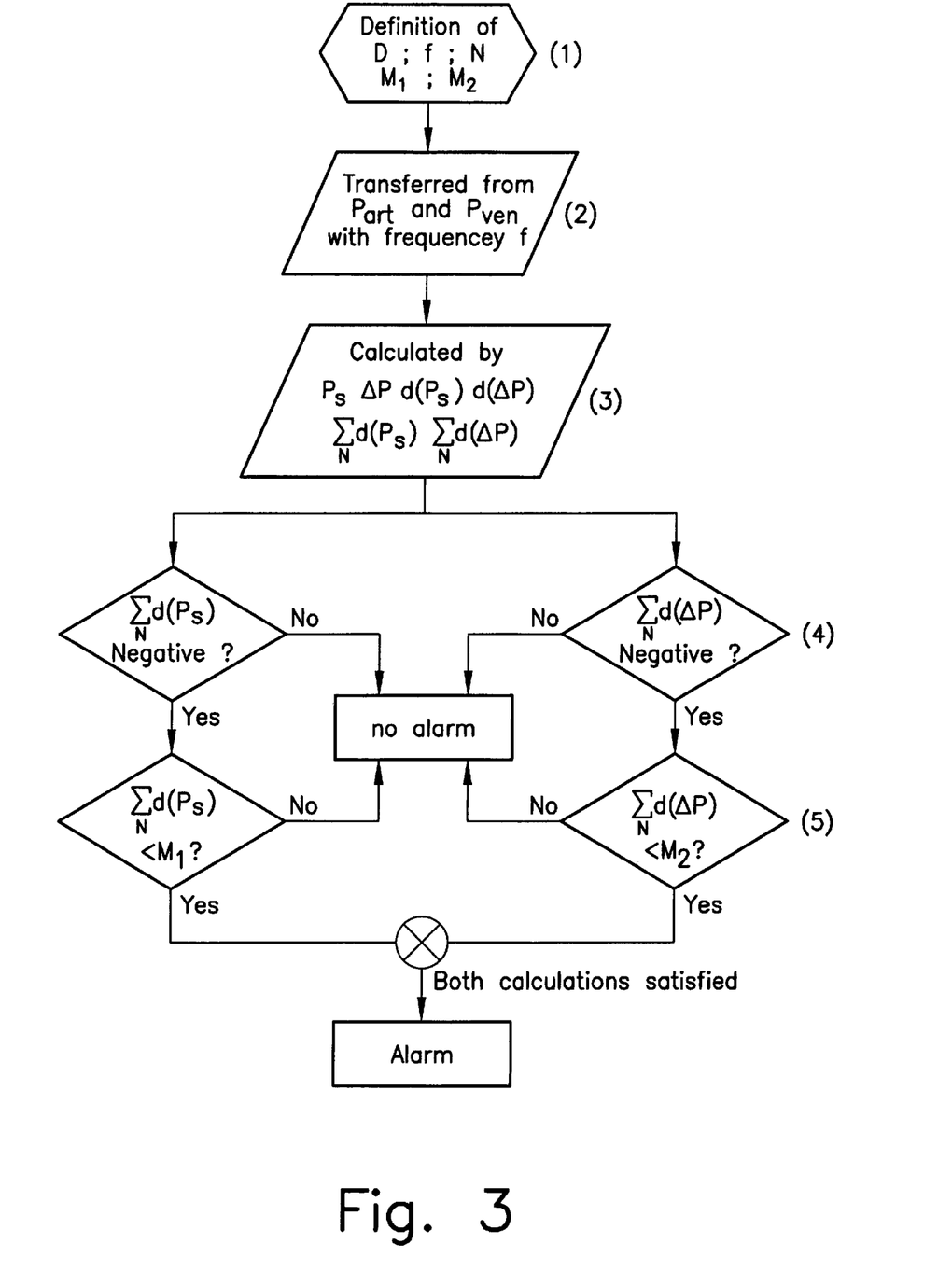
FIG. 3 is a flow chart depicting the monitoring device.

The functioning of monitoring device 17 is described in detail below with reference to FIG. 3.

The number N of successive measured values to be used for the analysis, the measurement frequency f and threshold values $M_1$ and $M_2$ are defined first. These values can be stored in memory unit 23 or they may be preset by the user (step 1).

The susceptibility of the protective system to faults, e.g., in short-term artificial pressure fluctuations, is reduced by analysis of N successive measured values. The value for N is an integer and depends on the frequency f with which the pressure values are determined. It can be adapted to the respective attenuation D of the pressure sensors. The following boundary condition applies to N:

$$N > f \cdot D \quad \text{(equation 9)}$$

At a typical measurement frequency f of ⅓ Hz, for example, and an attenuation of approximately 18 seconds, it should consequently hold that N>6. This guarantees that the pressure drop is detected completely.

The negative threshold values $M_1$ and $M_2$ characterize the sensitivity of the protective system. In general, the smaller the values of $M_1$ and $M_2$, the higher the threshold at which a machine alarm is triggered. To guarantee a response of the system, however, the values for $M_1$ and $M_2$ must be greater than the negative value of the venous pressure in the vascular access.

After the venous cannula slips out of the vascular access, the arterial fistula pressure drops slightly due to bleeding at the venous puncture site. This effect can be taken into account through a suitable choice of $M_2$, where the condition $M_1 < M_2$ must be met. Suitable values include, for example, $M_1 = -15$ mm Hg and $M_2 = -10$ mm Hg.

The response time tau of the protective system is given by the equation:

$$tau = N/f \quad \text{(equation 10)}$$

During the dialysis treatment, the arterial and venous pressures $P_{art}$, $P_{ven}$ are detected by pressure sensors 18, 19 at measurement frequency f in N successive measurements (step 2).

After each measurement, computer unit 22 calculates the sum $P_S$ of the venous and arterial pressures according to equation 1, and it calculates the difference (delta P) between the venous and arterial pressures according to equation 2. These values are stored in memory unit 23. Using equation 3, computer unit 22 calculates the difference, $d(P_S)$, between the sum $P_{SN}$ of the venous and arterial pressures of a subsequent measurement and the sum $P_{SN-1}$ of the venous and arterial pressures from a preceding measurement. Computer unit 22 calculates the difference, d(delta P), between the difference d (delta P) between the arterial and venous pressures from a preceding measurement delta $P_N$ and the difference delta $P_{N-1}$ between the arterial and venous pressures of a following measurement according to equation 4. These measured values are also stored in memory unit 23. The changes in sums, $d(P_S)$, of the N successive measurements are then added up by computer unit 22 according to equation 5 to form a first characteristic value $W_1$ for the condition of the vascular access. The changes in difference, d(delta P), are added up in computer unit 22 according to equation 6 to form a second characteristic value $W_2$ for the vascular condition (step 3).

Analyzer unit 25 checks the signs of the two characteristic values $W_1$, $W_2$. If either of the characteristic values $W_1$, $W_2$ is negative, no alarm is triggered (step 4). However, if both characteristic values $W_1$ and $W_2$ are negative, the characteristic values are then compared with the first and second threshold values $M_1$, $M_2$ (step 5).

For the case when $W_1$ is smaller than $M_1$ and $W_2$ is also smaller than $M_2$, analyzer unit 25 delivers an alarm signal to alarm unit 28. Alarm unit 28 preferably generates an acoustic and/or visual alarm and controls the control unit 16, which in turn stops blood pump 6 and closes the cutoff element 13. This guarantees that the patient will not be endangered in the event that venous cannula 7a slips out or there is a leak in venous blood line 7.

Similarly, a defective vascular condition can also be inferred according to equations 7 and 8 if both the first characteristic value $W_1$ and the second characteristic value $W_2$ are positive, and the first characteristic value $W_1$ is greater than a predetermined threshold value $M_3$ and the second characteristic value $W_2$ is greater than a predetermined threshold value $M_4$. In this case, the arterial cannula has slipped out or there is a blood leak in the arterial branch of the extracorporeal system.

Computer unit 22 with memory unit 23 and analyzer unit 25 may be parts of a microcomputer, such as are often present in known dialysis machines.

If the dialysis machine has an ultrafiltration device, the monitoring device can be deactivated within the first one to two minutes after the ultrafiltration device is turned on or off in order to prevent a false alarm.

The characteristic principles which form the basis of the method of monitoring the vascular access according to the present invention are explained below.

The arterial and venous pressures $P_{art}$ and $P_{ven}$ measured in the extracorporeal system are composed of the dynamic pressure in the extracorporeal system produced by the flow of the blood pump and the dynamic pressure in the patient's vascular access.

The dynamic pressure in the extracorporeal system is a function of the extracorporeal blood flow and the sum of the flow resistances in the extracorporeal system. Since the arterial and venous flow resistance differ due to the difference in geometry of the components through which the flow passes, the pressure sum $P_S$ is also a function of the blood flow.

As a rule, the delivery rate $Q_B$ of the blood pump is set at a fixed value in the known blood purification methods. Thus, the sum of the flow resistances in the extracorporeal system is also constant at a constant viscosity of the blood. An increase in viscosity, e.g., due to ultrafiltration, leads to a reduction in the reduced arterial pressure and to an increase in the excess venous pressure in the long run. Consequently, the pressure response with a steady increase in viscosity is identical to a slight increase in blood flow.

Figure 4:
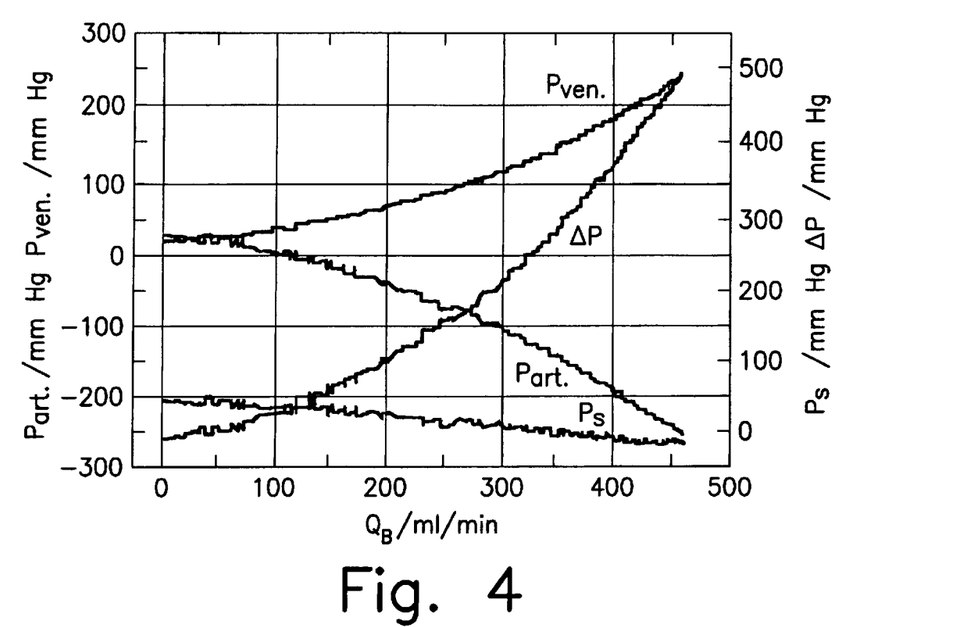
FIG. 4 shows arterial or venous pressure as a function of the blood flow in the extracorporeal system.

FIG. 4 shows the extracorporeal pressures as a function of blood flow $Q_B$ at a constant viscosity (fistula flow $Q_F$=1255 mL/min, arterial fistula pressure $P_{F\ art}$=27 mm Hg, venous fistula pressure $P_{F\ ven}$=17 mm Hg).

The above measurements and all the following measurements were performed during a simulated dialysis treatment. The vascular access was a segment of tubing with an inside diameter of 8 mm connected to a gear pump. To measure the flow within the vascular access, a Doppler flow meter was used. The arterial and venous pressures within the vascular access ($P_{Fistel}$) were checked with two pressure manometers and were adjusted with two hose clamps. Water was used in all the measurements (T=37 degrees C). The cannulas used to puncture the vessels were connected to the dialysis machine by two conventional tubing systems.

The dynamic pressure in the patient's vascular access, hereinafter referred to as the fistula pressure, is also a function of the viscosity of the blood, the systemic blood pressure and the systemic vascular flow resistances. The fistula pressure is thus a patient-specific parameter and also depends on the type of vascular access, the viscosity of the blood and the vascular system supplying blood to the vascular access. By analogy, with the dynamic pressure in the extracorporeal system, a change in the fistula pressure, e.g., due to fluctuations in blood pressure, an increase in viscosity or a change in position of the patient, leads to a change in the arterial and venous pressure values.

Figure 5:
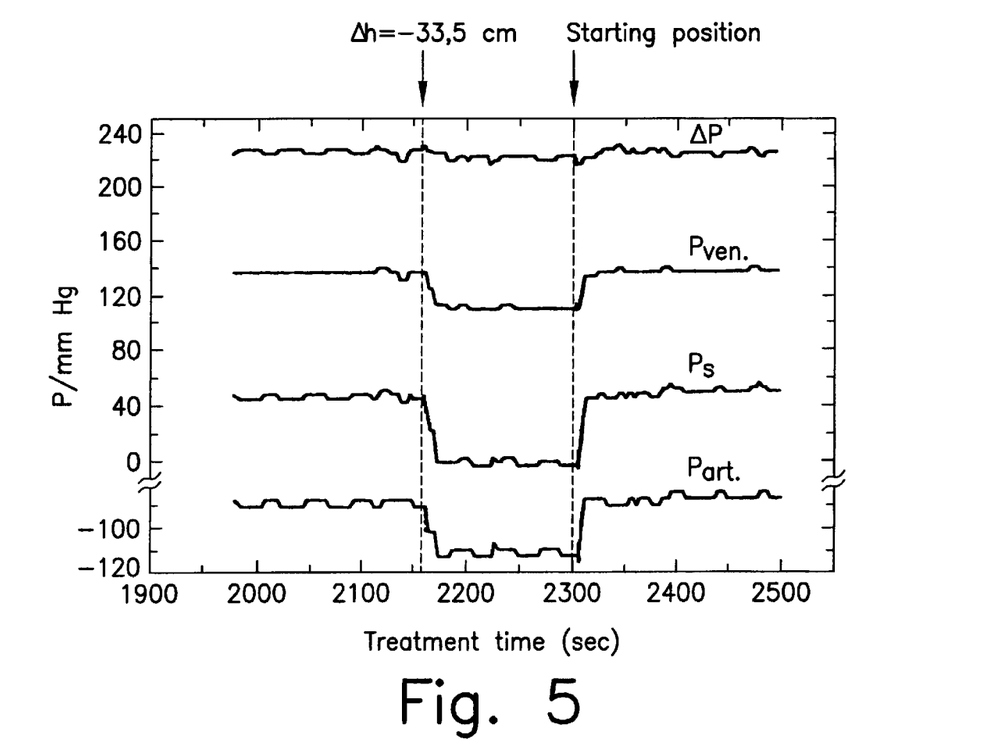
FIG. 5 depicts change in arterial and venous pressure in the extracorporeal system with a change in position of the patient.

FIG. 5 shows the behavior of the extracorporeal pressures at a constant effective blood flow rate $Q_B$ when the patient's position changes by delta h=−33.5 cm relative to the extracorporeal pressure sensors ($Q_B$=300 mL/min, $Q_F$=1252 mL/min; pressure in the vascular access: $P_{F\ art}$=27 mm Hg, $P_{F\ ven}$=17 mm Hg). This is the case, for example, when the patient lies down or lowers his recliner. This reduces the arterial and venous pressure values by the amount of the hydrostatic pressure difference (approximately 0.78 mm Hg per cm of height difference between the pressure sensor and the fistula). Since the arterial and venous pressures in the extracorporeal system change by the same value when the patient changes positions, the pressure difference delta P remains constant. However, the sum of the pressures $P_S$ drops by two times the amount of the hydrostatic pressure difference.

This behavior is manifested (although in a diminished form) even with a pressure drop during the treatment. In this case, the arterial and venous pressures in the extracorporeal system also drop.

Figure 6:
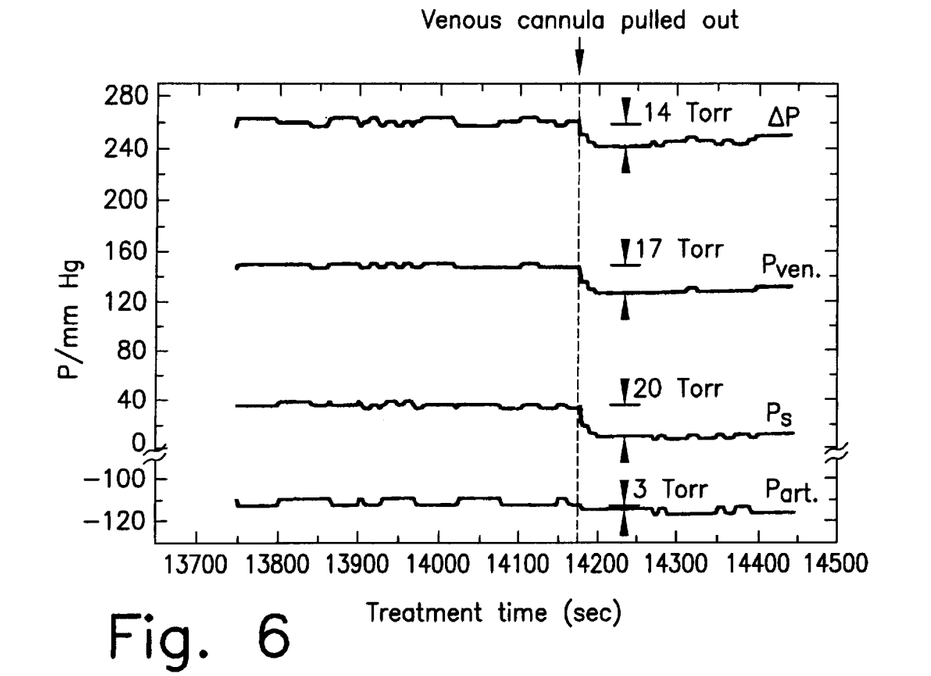
FIG. 6 demonstrates pressure relationships in the extracorporeal system when a venous cannula slips out of the vascular access.

FIG. 6 shows the pressure relationships when the venous dialysis cannula slips out of the patient's fistula ($Q_B$=300 mL/min, $Q_F$=1254 mL/min, $P_{F\ art}$=27 mm Hg, $P_{F\ ven}$=17 mm Hg). The pressure at the venous sensor of the extracorporeal system ($P_{ven}$) drops by the amount of the venous fistula pressure within about 15–20 seconds. The delay time is determined by the electronic attenuation of the extracorporeal pressure signals. The arterial pressure value ($P_{art}$) is reduced only slightly within the first minutes, as explained below.

The blood loss which is caused by the open venous puncture site and leads to the drop in fistula pressure can be estimated roughly on the basis of the law of conservation of energy:

$$P \cdot V = \frac{1}{2} M \cdot v^2 \qquad \text{(Equation 11)}$$

where the following abbreviations are used:
P: pressure
V: volume
M: mass
v: velocity With V=M/rho, it follows for the velocity of the blood stream from the open puncture site:

$$v = \sqrt{\frac{2P}{\rho}} \qquad \text{(Equation 12)}$$

where:
rho=density

At a venous fistula pressure of 17 mm Hg (=22.6 mbar) and a blood density of 1.0506 g/cm³ (37 degrees C.), the velocity of the stream is approximately 2.1 m/s. Under the assumption of a uniform opening of the puncture site, the volume flow with a cylindrical stream profile is given by the equation:

$$Q = \pi r^2 \cdot v \qquad \text{(Equation 13)}$$

With a typical cannula diameter of 1.6, a value of approximately 250 mL/min (=⅕ of the fistula flow) is obtained. The open puncture site swells in vivo, so the effective diameter of the hole will be smaller than the diameter of the cannula. Thus, the stated value is to be regarded as an upper limit.

Because pressure and flow are proportional, the venous fistula pressure is reduced by 17/5=3.4 mm Hg (Hagen-Poiseuille law). Due to the reduced venous fistula pressure, the extracorporeal arterial pressure drops by the same amount. However, since the change in arterial pressure is always smaller than the change in venous pressure, both $P_S$ and delta P are reduced.

Figure 7:
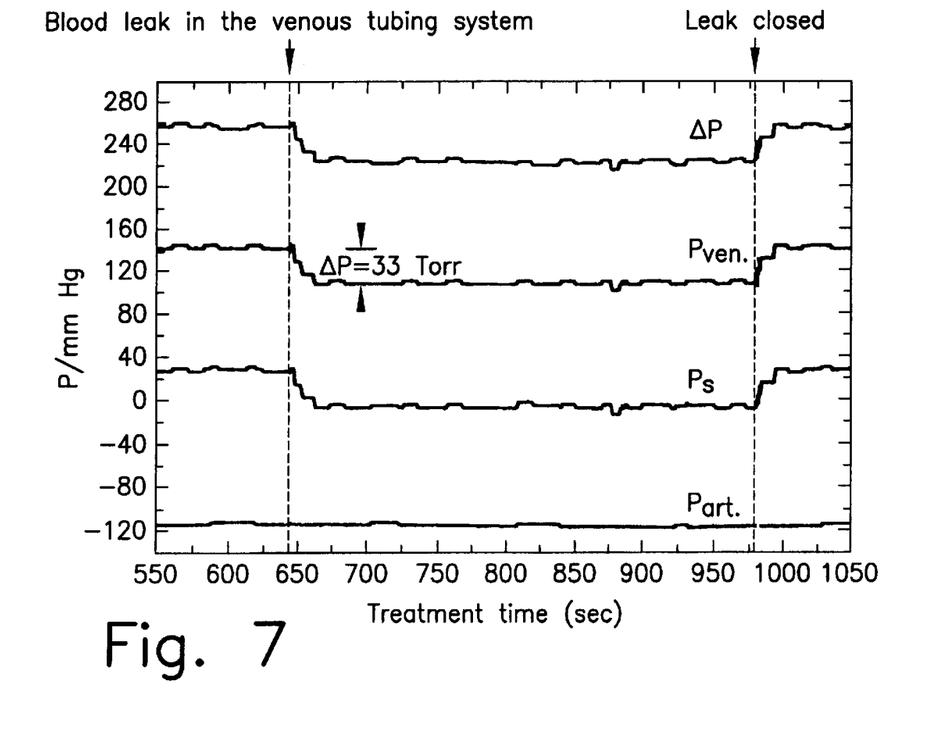
FIG. 7 demonstrates pressure relationships when there is a blood leak in the venous branch of an extracorporeal system.

FIG. 7 shows the pressure relationships when there is a blood leak in the venous tubing system. The venous tubing was punctured with an injection cannula below the drip chamber ($Q_B$=300 mL/min, $Q_F$=1250 mL/min, $P_{F\ art}$=27 mm Hg, $P_{F\ ven}$=17 mm Hg, leakage rate 50 mL/min). The pressure at the venous sensor drops by approximately 33 mm Hg within approximately 15–20 sec at a leakage rate of 50 mL/min. However, there is no significant change in the arterial pressure. By analogy with FIG. 6, both delta P and $P_S$ drop. Consequently, the changes in totals according to equations 6 and 7 are negative in both cases.

What is claimed is:

1. A system for extracorporeal blood treatment comprising:
   (a) an extracorporeal blood path comprising an arterial line in fluid communication with a first vascular access and an inlet to a blood treatment device, and a venous line in fluid communication with an outlet of the blood treatment device and with a second vascular access;
   (b) an arterial fluid pressure sensor in communication with the arterial line and constructed and arranged for measuring pressure within the arterial line;
   (c) a venous fluid pressure sensor in communication with the venous line and constructed and arranged for measuring pressure within the venous line;
   (d) a computer unit connected to the arterial and venous pressure sensors, which is constructed and arranged for generating first and second characteristic values for the integrity of the vascular access from measured arterial and venous pressures;
   (e) an analyzer unit constructed and arranged for analyzing the integrity of the vascular access by comparing the first and second characteristic values to first and second ranges of predetermined values.

2. The system of claim 1, wherein generating the first characteristic value includes calculating a sum of the measured pressure in the venous line and the measured pressure in the arterial line according to the equation $P_S=P_{VEN}+P_{ART}$, and generating the second characteristic value includes calculating a difference between the measured pressure in the venous line and the measured pressure in the arterial line according to the equation $\Delta P=P_{VEN}-P_{ART}$.

3. The system of claim 2, further comprising a memory unit connected to the computer unit, which is constructed and arranged for storing successive pressure sum and pressure difference values calculated by the computer unit and transmitting the stored values to the computer unit.

4. The system of claim 3, wherein generating the first characteristic value further includes calculating a change in the pressure sum for successive measurements by subtracting the sum for a first measurement from the sum for a second measurement, and generating the second characteristic value further includes calculating a change in the pressure difference between successive measurements by subtracting the difference for a first measurement from the difference for a second measurement.

5. The system of claim 4, wherein the first characteristic value is calculated by adding the changes in the sum of a predetermined number of successive measurements, and the second characteristic value is calculated by adding the changes in the predetermined number of calculated pressure differences.

6. The system of claim 1, wherein the analyzer unit is further constructed and arranged for generating a safe response in reaction to characteristic values selected from the group consisting of:
   (i) a first characteristic value below the first range of values, and a second characteristic value below the second range of values, and
   (ii) a first characteristic value above the first range of values, and a second characteristic value above the second range of values.

7. The system of claim 6, wherein the smallest value in the first range of predetermined characteristic values ($M_1$) is less than the smallest value in the second range of predetermined characteristic values ($M_2$).

8. The system of claim 7, wherein $M_1$ is −15 mmHg and $M_2$ is −10 mmHg.

9. The system of claim 6, wherein the predetermined number of successive measurements is greater than a product of the frequency of arterial and venous pressure measurement and a value for the attenuation of the arterial and venous pressure sensors.

10. The method of claim 7, wherein the safe response is an alarm selected from the group consisting of visual and audible alarms.

11. The method of claim 7, wherein the safe response comprises closing a cutoff clamp in the venous line.

12. The method of claim 7, wherein the safe response comprises interrupting the provision of blood to the extracorporeal blood path.

13. The method of claim 7, wherein the safe response comprises stopping a blood pump provided in the arterial line.

14. The system of claim 2, wherein the system is incorporated into a dialysis machine.

* * * * *

UNITED STATES PATENT AND TRADEMARK OFFICE
CERTIFICATE OF CORRECTION

PATENT NO. : 6,221,040 B1
DATED : April 24, 2001
INVENTOR(S) : Wolfgang Kleinekofort It is certified that error appears in the above-identified patent and that said Letters Patent is hereby corrected as shown below:

<u>Column 10,</u>
Line 34, change "6" to -- 5 --.
Lines 39, 42, 44 and 47, change "7" to -- 6 --.
Line 50, change "2" to -- 1 --.

Signed and Sealed this

Second Day of July, 2002

Attest:

Attesting Officer

JAMES E. ROGAN
Director of the United States Patent and Trademark Office